United States Patent
Chiou et al.

(10) Patent No.: US 12,091,677 B2
(45) Date of Patent: Sep. 17, 2024

(54) CARBOXYLATED NANODIAMOND-MEDIATED CRISPR-CAS9 DELIVERY SYSTEM

(71) Applicants: Taipei Veterans General Hospital, Taipei (TW); National Chiao Tung University, Hsinchu (TW); National Cheng Kung University, Tainan (TW)

(72) Inventors: Shih-Hwa Chiou, Taipei (TW); Tien-Chun Yang, Taipei (TW); Chia-Ching Chang, Hsinchu (TW); Yon-Hua Tzeng, Tainan (TW)

(73) Assignees: Taipei Veterans General Hospital, Taipei (TW); National Chiao Tung University, Hsinchu (TW); National Cheng Kung University, Tainan (TW)

( * ) Notice: Subject to any disclaimer, the term of this patent is extended or adjusted under 35 U.S.C. 154(b) by 355 days.

(21) Appl. No.: 17/071,667

(22) Filed: Oct. 15, 2020

(65) Prior Publication Data

US 2021/0108230 A1    Apr. 15, 2021

Related U.S. Application Data

(60) Provisional application No. 62/915,143, filed on Oct. 15, 2019.

(51) Int. Cl.
*C12N 15/90* (2006.01)
*A61K 9/51* (2006.01)
*C12N 9/22* (2006.01)
*C12N 15/11* (2006.01)

(52) U.S. Cl.
CPC .......... *C12N 15/907* (2013.01); *A61K 9/5115* (2013.01); *C12N 9/22* (2013.01); *C12N 15/11* (2013.01); *C12N 2310/20* (2017.05); *C12N 2800/80* (2013.01)

(58) Field of Classification Search
CPC ........ C12N 15/907; C12N 9/22; C12N 15/11; C12N 2310/20; C12N 2800/80; C12N 15/87; C12N 15/111; C12N 2320/32; A61K 9/5115; A01K 2217/072; A01K 2227/105; A01K 2267/0306
See application file for complete search history.

(56) References Cited

PUBLICATIONS

Chu et al. "Development of a Growth-Hormone-Conjugated Nanodiamond Complex for Cancer Therapy." ChemMedChem 9.5 (2014): 1023-1029 (Year: 2014).*
Burnight et al. "Using CRISPR-Cas9 to generate gene-corrected autologous iPSCs for the treatment of inherited retinal degeneration." Molecular Therapy 25.9 (2017): 1999-2013 (Year: 2017).*
Molday et al. "X-linked juvenile retinoschisis: clinical diagnosis, genetic analysis, and molecular mechanisms." Progress in retinal and eye research 31.3 (2012): 195-212 (Year: 2012).*
Tzeng et al. "Superresolution imaging of albumin-conjugated fluorescent nanodiamonds in cells by stimulated emission depletion." Angewandte Chemie International Edition 50.10 (2011): 2262-2265 (Year: 2011).*
Duan et al. "Quantum dots with multivalent and compact polymer coatings for efficient fluorescence resonance energy transfer and self-assembled biotagging." ChemiStry of materialS 22.15 (2010): 4372-4378 (Year: 2010).*

* cited by examiner

*Primary Examiner* — Jeremy C Flinders
*Assistant Examiner* — Alexander W Nicol
(74) *Attorney, Agent, or Firm* — Birch, Stewart, Kolasch & Birch, LLP

(57) ABSTRACT

The present invention provides a carboxylated nanodiamond-mediated CRISPR-Cas9 delivery system for gene editing comprising nanodiamond (ND) particles as the carriers of CRISPR-Cas9 components designed to introduce the mutation in a given gene for repairing a tissue damage.

16 Claims, 13 Drawing Sheets
(11 of 13 Drawing Sheet(s) Filed in Color)
Specification includes a Sequence Listing.

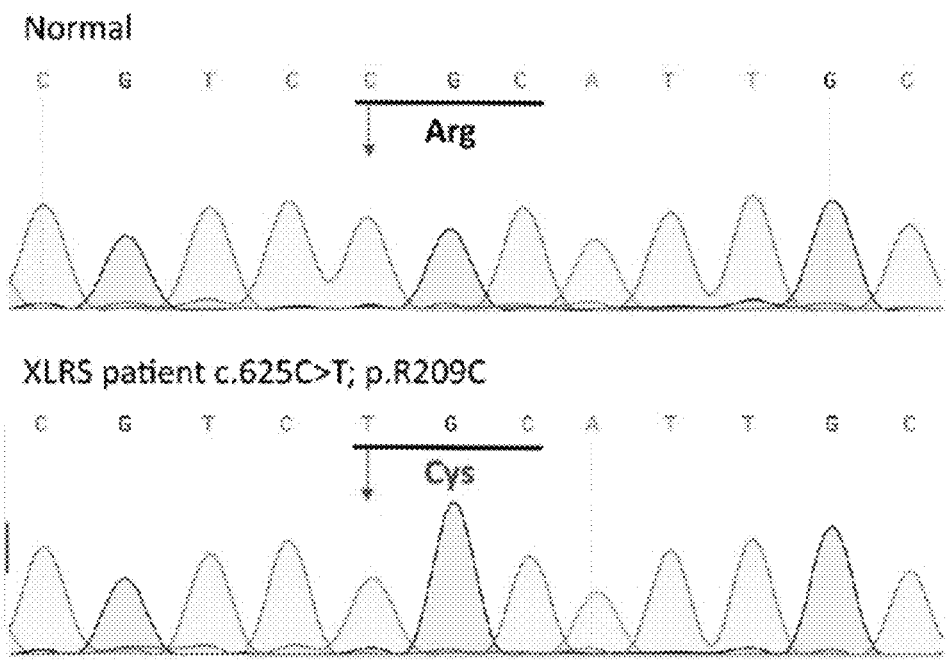
*Fig. 1A*
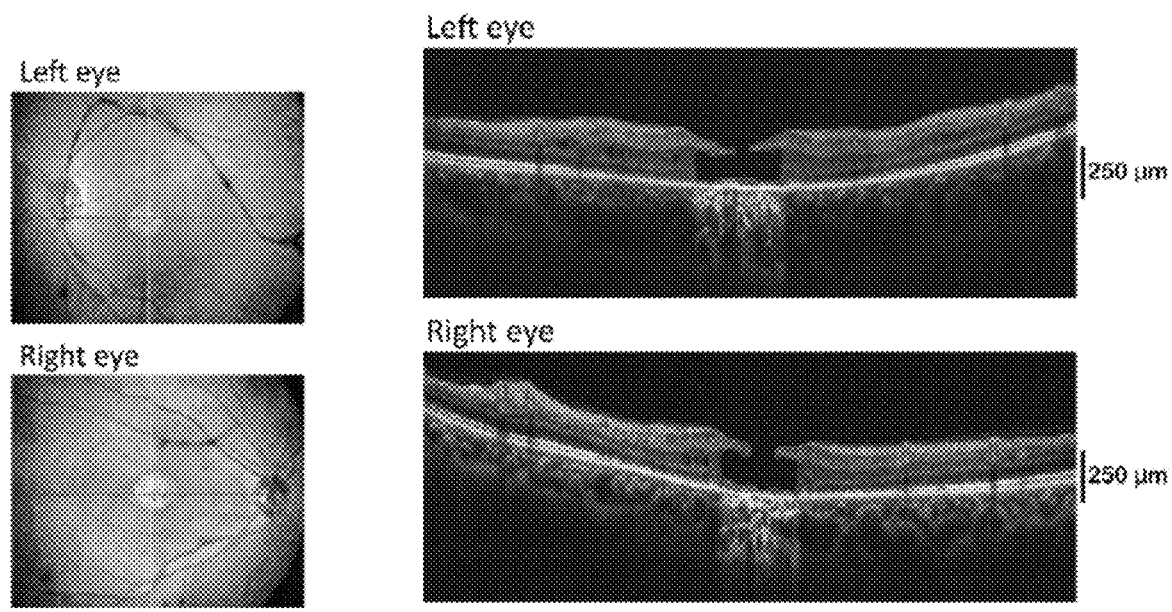
*Fig. 1B*  *Fig. 1C*

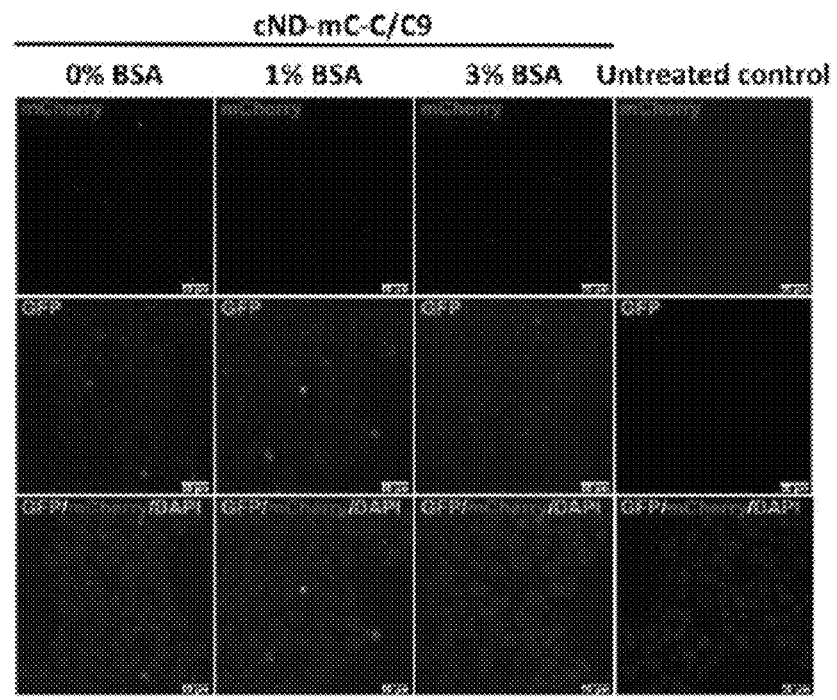
*Fig. 3A*
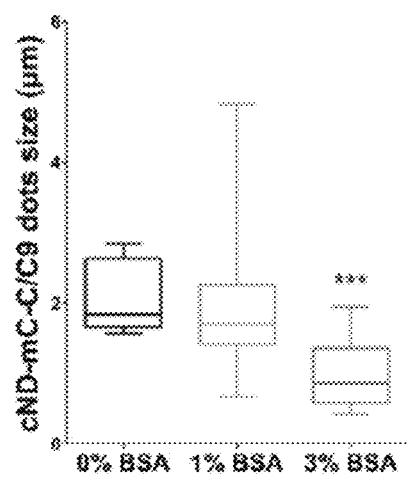 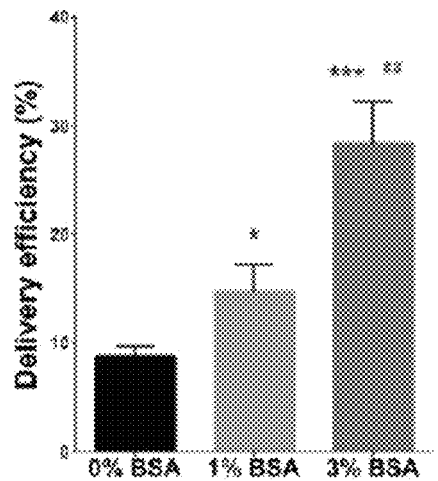
*Fig. 3B*  *Fig. 3C*

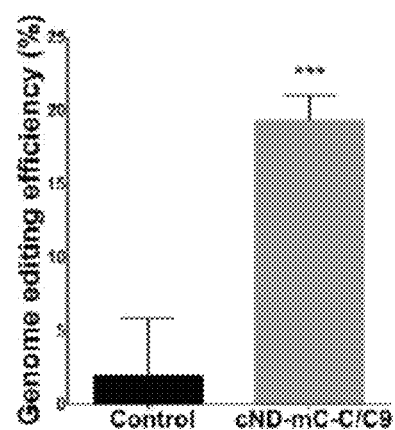
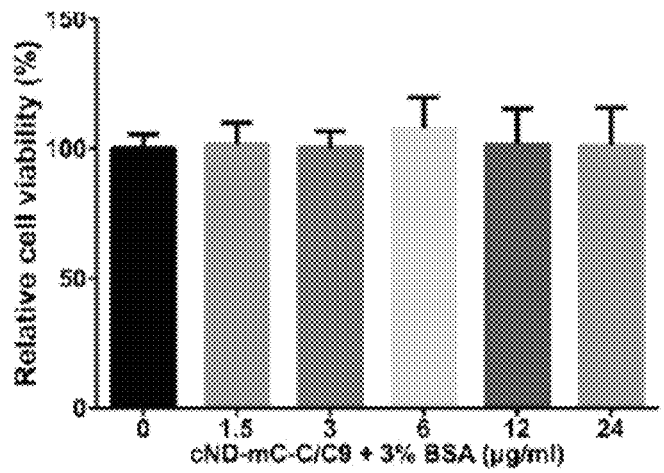
*Fig. 3D*  *Fig. 3E*

CARBOXYLATED NANODIAMOND-MEDIATED CRISPR-CAS9 DELIVERY SYSTEM

REFERENCE TO SEQUENCE LISTING SUBMITTED VIA EFS-WEB

This application includes an electronically submitted sequence listing in .txt format. The .txt file contains a sequence listing entitled "2020-12-16_5992-0297PUS2_ST25" created on December 16, 2020 and is 3,240 bytes in size. The sequence listing contained in this .txt file is part of the specification and is hereby incorporated by reference herein in its entirety.

FIELD OF THE INVENTION

The present invention pertains to a CRISPR-Cas9 delivery System for delivering some components for treating a disease or repairing a tissue damage.

BACKGROUND OF THE INVENTION

X-linked juvenile retinoschisis (XLRS) is a common hereditary macular degeneration that affects the vision of young boys, with a prevalence of 1 in 5,000 to 1 in 25,000 [1, 2]. The clinical features of XLRS include early vision loss associated with bilateral foveae and splitting of the inner retinal layer, retinal detachment, and vitreous hemorrhage [3]. RS1, the gene associated with XLRS, contains six exons and encodes a protein of 224 amino acids [4]. More than one hundred RS1 mutations have been confirmed to be associated with the development of XLRS, and this result also indicates a high degree of clinical variability (http://www.dmd.nl/rs).

The protein structure of RS1 is composed of N-terminal secretory leader sequence and discoidin domain in C-terminal region, which are highly conserved across species [5, 6]. The discoidin domain is found in a number of secreted or membrane-bound proteins and is known to be involved in cell adhesion and cell-cell interaction [7]. Most of the mutations in the RS1 gene are missense mutations, although nonsense mutations, deletions, insertions, and splice site mutations are also found [8, 9]. Previous studies have indicated that the patients with RS1 missense mutations Asp145His, Arg102Gln, Arg209His and Arg213Gln exhibit severe retinoschisis characteristics in the clinic [10, 11]. Missense mutations in the RS1 protein cause misfolding and may cause intracellular and extracellular protein accumulation, ultimately leading to cystic and schisis structures in the retina [12]. RS1 is expressed and secreted by photoreceptors of the outer retina and bipolar cells of the inner retina, as was observed in the retina of mice [13]. Further studies have shown that RS1 attaches to the surface of retinal cells after synthesis and secretion by photoreceptors and mediates adhesion between photoreceptor cells, bipolar cells and Muller cells, thereby promoting the maintenance of structural integrity of the retina [14].

Nanodiamond (ND) is a carbon-based nanomaterial that can be used to carry biomolecules and chemicals [15-17]. In order to achieve the goal of multi-functional delivery by NDs, several techniques have been developed to promote conjugation of chemicals to the surface by introducing carboxyl, hydroxyl and thiol groups. Many studies have reported that NDs can also be used as a delivery system for biomolecules, such as DNA [18, 19], proteins [20, 21], and small molecule drugs [22, 23]. ND's biocompatibility and non-toxicity makes it a relatively safe nanomaterial for biomedical applications [24]. These advantages of NDs make it a promising carrier of therapeutic agents to treat hereditary retinal diseases.

The application of NDs for the treatment of human diseases is promising, but the U.S. Food and Drug Administration (FDA) still requires that the agents injected into the body do not accumulate for long periods of time [25]. Although fluorescently labeled NDs have an advantage of a stable fluorescent signal, a larger particle diameter is required to maintain the fluorescent sensitivity [26]. Animal experiments uncovered that larger sized particles may accumulate in organs, even without significant toxicity [27, 28]. The turnover of nanoparticles is an important issue in clinical applications. The production of urine by a kidney is an important way to eliminate them [29]. The threshold for the inorganic nanoparticles to filter molecules through the glomerular capillary wall is about 5.5 nm. Therefore, the size of the NDs may affect the efficiency of renal clearance [30].

It is desirable to develop a delivery system using a safe, efficient and traceable nanocarriers.

BRIEF DESCRIPTION OF THE DRAWINGS

The patent or application file contains at least one color drawing. Copies of this patent or patent application publication with color drawing will be provided by the USPTO upon request and payment of the necessary fee. The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1A, FIG. 1B and FIG. 1C show the clinical characteristics of RS1 c.625C>T mutation carrier patient with X-linked juvenile retinoschisis (XLRS). FIG. 1A (SEQ ID NOS: 5 and 6) shows the sanger sequencing results of the mutated RS1 locus in normal individual (top) and XLRS patient (bottom). The c.625C>T mutation in exon 6 of RS1 results in arginine to cysteine substitution. FIG. 1B provides the ophthalmoscopy images of the eyes of XLRS patient showing a clear area of the chorioretinal atrophy involving the fovea. FIG. 1C provides the OCT images revealing the presence of large cysts indicative the retinal degeneration FIG. 2A FIG. 2E provides the FTIR spectra of the ND samples: cND (green line), cND-mC (blue line) and cND-mC-C/C9

(brown line).

FIG. 3A-FIG. 3E provide the editing of RS1 gene by cND-mC-C/C9 in hiPSCs. FIG. 3A provides fluorescence microscopy images of hiPSCs treated with cND-mC-C/C9 nanoparticles mixed with the indicated concentrations of BSA. FIG. 3B shows the measurement of the diameter of mCherry fluorescent dots inside hiPSCs on fluorescence microscopy images using ImageJ software. The means values are shown with standard deviation error bars. FIG. 3C shows the quantification of delivery efficiency of cND-mC-C/C9 nanoparticles mixed with different concentrations of BSA. Expressed as the mean percentage of cells with internalized mCherry signal. FIG. 3D provides ddPCR analysis of RS1 c.625C>T copy number in GFP-sorted population of cND-mC-C/C9-treated hiPSCs. FIG. 3E provides the results of the CCK-8 cell viability assay showing the effect of treatment of hiPSCs with the indicated concentrations of cND-mC-C/C9affect their viability (Data expressed as relative to untreated (0 µg/ml). Statistical data shown as the means ±standard deviation error bars, *p<0.05, ***p<0.001, ##p<0.01 Student's t-test from 3 independent experiments. * versus 0% BSA, #3% BSA versus with 1% BSA).

FIG. 4A provides the SLO fundus image in mouse eyes injected with cND-mC-C/C9 nanoparticles carrying Cas9-GFP (Cas9 only) and RS1-sgRNA (Cas9+sgRNA) DNA constructs. FIG. 4B provides Fluorescence microscopy observation of localization of mCherry and green fluorescent protein (GFP) signals in transverse section of cND-mC-C/C9-treated mouse retina. GFP and mCherry signals are indicated by arrows. FIG. 4C provides Fluorescence microscopy observation of expression of GFP expression in transverse section of cND-mC-C/C9-treated mouse retina. GFP signals were observed in RGC layer (yellow arrows), photoreceptor/Müller cell layer (red arrows), and RPE layer (white arrowheads). Recoverin, the marker of photoreceptors, is immunostained in red. Nuclei stained with DAPI. FIG. 4D provides H&E staining of the section of cND-mtwC-C/C9-treated mouse retina. RPE—retinal pigment epithelium, PR—photoreceptors, ONL—outer nuclear layer, OPL—outer plexiform layer, INL—inner nuclear layer, IPL—inner plexiform layer, RGC—retinal ganglion cells.

FIG. 5A (SEQ ID NOS: 10, 11, 12 and 13) provides the scheme showing the design of CRISPR-Cas9 constructs to introduce c.625C>T mutation into the mouse Rs1 gene. The fragment of Rs1 exon 6 sequence containing the cleavage site (red arrowhead) and PAM sequence (red font) shown at the top. The maps of two DNA constructs, Cas9-GFP and Rs1-sgRNA, shown at the bottom. FIG. 5B shows the results of the ddPCR analysis of Rs1 c.625C>T copy number in retinas treated for two weeks with control (Cas9 only) and Rs1-targeting cND-mC-C/C9 nanoparticles (Cas9+sgRNA). Data are expressed as relative to control. FIG. 5C provides OCT images of mouse retinas treated for two weeks with control (Cas9 only) and (Cas9+sgRNA) cND-mC-C/C9 nanoparticles. Retinal layers shown to the right: GCL—ganglion cell layer, IPL—inner plexiform layer, INL—inner nuclear layer, ONL—outer nuclear layer, OPL—outer plexiform layer, OLM outer limiting membrane, IS—inner segments, OS—outer segments, RPE—retinal pigment epithelium. Bottom image: zoom in of the area of the top image surrounded by red rectangle, showing the structure of hyperreflective outer retinal bands 2 and 3. FIG. 5D provides the quantification of thickness of hyperreflective outer retinal bands 2 and 3 in OCT images in FIG. 4C. The data expressed as means vale measurements, "Cas9+sgRNA" quantified relative to "Cas9 only" control.

FIG. 6A shows Immunostaining with antibodies against cone cell-specific opsins (Opsin) and RS1. FIG. 6B shows the immunostaining with antibodies against recoverin and rhodopsin. FIG. 6C shows the quantification of the length of immunofluorescent signals of cone cell-specific opsins.

SUMMARY OF THE INVENTION

Figure 2A:
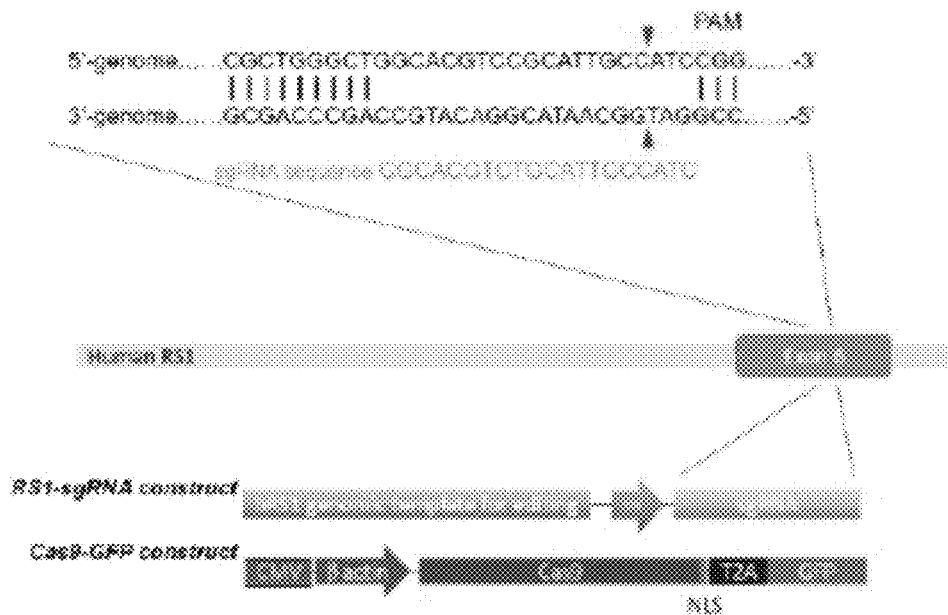
FIG. 2A (SEQ ID NOS: 7, 8, and 9) provides the schematic showing the design of CRISPR-Cas9 constructs to introduce c.625C>T mutation into the human RS1 gene. The fragment of RS1 exon 6 sequence containing the cleavage site (red arrowhead) and PAM sequence (red font) shown at the top. The maps of two DNA constructs, Cas9-GFP and RS1-sgRNA, shown at the bottom.

Accordingly, the present invention provides a highly efficient delivery system for gene editing.

In one aspect, the present invention provides a delivery system for gene editing comprising nanodiamond (ND) particles as the carriers of CRISPR-Cas9 components including a Cas9 protein, a guide protein guide RNA (gRNA), a template DNA designed to introduce the mutation in a given gene for repairing a tissue damage, wherein the ND particles have a diameter less than 5 nm, and functionalized by carboxylation of the surface and covalently conjugated with a flurescent fluorescent protein; and a first linear DNA centruet construct for expression of the Case-9 Cas9 protein, and a second linear DNA centruet construct for expression of the gRNA/template DNA linked with the ND particles covalently conjugated with the flurescent fluorescent protein by phosphoryl imidazole to obtain carboxylated nanodiamond-mediated CRISPR-Cas9 ND particles.

In one example of the invention, the ND particles have a diameter in a range of 3 nm-5 nm; preferably the ND particles have a diameter of about 3 nm.

In one example, the fluorescent protein as used in the invention is a mCherry protein.

In one particular example, the carboxylated nanodiamond-mediated CRISPR-Cas9 ND particles according to the invention may be coated by bovine serum albumin (BSA) before using. It was unexpectedly found that the delivery efficiency of NDs is increased and the diameter of of mCherry fluorescent dots, indicative of less aggregated state, is decreased.

In one example, the given gene is RS1 gene associated with X-linked retinoschisis (XLRS).

According to the invention to create a disease model, the mutation in the given gene is introduced via two linear DNA constructs, which are attached to the conjugated mCherry, and the first linear DNA construct encodes for Cas9 endonuclease and a green fluorescent protein (GFP) reporter, and the second linear DNA construct encodes for a sgRNA and contains an insert of HDR template designed to introduce RS1 c.625C>T mutation.

In the invention, the the delivery leads to introduction of RS1 c.625C>T mutation in human iPSCs or mouse retinas.

In another aspect, the invention provides a method for treating a disease or repairing a tissue damage in a subject, comprising delivering and internalizing the mutation in a given gene into said subject through the system of the invention.

In one example, the disease is X-linked retinoschisis (XLRS), and the given gene is RSI gene associated with X-linked retinoschisis (XLRS).

In a further aspect, the invention provides a method for creating an in vitro or in vivo disease model, comprising delivering and internalizing the mutation in a given gene into induced pluripotent stem cells (iPSCs) or an animal organ through the system of the invention.

In one example, the disease is X-linked retinoschisis (XLRS), the given gene is RSI gene associated with X-linked retinoschisis (XLRS), and the animal organ is mouse retinas.

In one example of the invention, the delivery leads to an introduction of RS1 c.625C>T mutation into human iPSCs or mouse retinas.

According to the invention, the Rs1 gene editing in the mouse retinas results in several pathological features typical for XLRS, such as aberrant photoreceptor structure.

It is to be understood that both the foregoing general description and the following detailed description are exemplary and explanatory only and are not restrictive of the invention.

DETAILED DESCRIPTION OF THE INVENTION

Unless defined otherwise, all technical and scientific terms used herein have the same meaning as commonly understood by a person skilled in the art to which this invention belongs.

Nanodiamond (ND) particles can be used as a drug delivery vehicle characterized by high biocompatibility, loading capacity and cell penetration. The non-covalent methods of ND-oligonucleotide conjugation can be used to prepare the NDs, and the covalent bond of the nucleic acid through the peptide contributes to the stability, accessibility and selectivity of the conjugate. In the present invention, the ND-based CRISPR-Cas9 delivery vector was designed by functionalizing ND surface with a carboxyl (COOH) group, conjugating 6His-tagged mCherry reporter protein to the ND via the peptide bond, and covalently attaching linear DNA encoding green fluorescent protein (GFP) reporter and components of CRISPR-Cas9 system via the phosphoryl imidazole bond between 5'-phosphate of DNA and imidazole group of histidine of 6His-tag. Since internalization of nanoparticles usually undergoes via the endosome pathway, mCherry was chosen to construct the backbone of the delivery vector to monitor the transfection efficiency, because it constitutively exhibits red fluorescence even in the acidic environment (pH 5-6) of the late endosomes, unlike GFP, whose green fluorescence is quenched at such pH values. At the same time, GFP was designed to be expressed from a conjugated DNA, as a reporter of successful delivery and functional effects of cargo DNA.

As used herein, the term "nanodiamonds (NDs)," "nanodiamond (ND) particles" or "diamond nanoparticles" refers to particles having a shape of diamond with a size below 1 micrometre, which can be produced by impact events such as an explosion or meteoritic impacts, and are potential for surface functionalization. As being inexpensive, large-scale synthesis, they are potential for surface functionalization. the ND particles can be used as a drug/biomaterial delivery vehicle characterized by high biocompatibility, loading capacity and cell penetration. The non-covalent methods of ND-oligonucleotide conjugation can be used to prepare the NDs, and the covalent bond of the nucleic acid through the peptide contributes to the stability, accessibility and selectivity of the conjugate.

In one example of the present invention, the ND-based CRISPR-Cas9 delivery vector was designed by functionalizing ND surface with a carboxyl (COOH) group, conjugating 6His-tagged mCherry reporter protein to the ND via the peptide bond, and covalently attaching linear DNA encoding GFP reporter and components of CRISPR-Cas9 system via the phosphoryl imidazole bond between 5'-phosphate of DNA and imidazole group of histidine of 6His-tag. Since internalization of ND particles usually undergoes via the endosome pathway, mCherry was chosen to construct the backbone of the delivery vector to monitor the transfection efficiency, because it constitutively exhibits red fluorescence even in the acidic environment (pH5-6) of the late endosomes, unlikeGFP, whose green fluorescence is quenched at such pH values. At the same time, GFP was designed to be expressed from a conjugated DNA, as a reporter of successful delivery and functional effects of cargo DNA. We demonstrated that the mCherry protein carried by cNDs was stable in the mouse retina for up to two weeks. In addition, the GFP reporter gene was also continuously expressed in vivo from plasmid DNA. In order to ensure more efficient transfection by nanocarriers, they often need to be stabilized with additional materials.

It was found in the present invention that bovine serum albumin (BSA) increased delivery efficiency of cNDs in a concentration dependent manner, as well as decreased the diameter of mCherry fluorescent dots, indicative of less aggregated state (see FIG. 3).

CRISPR-Cas9-mediated genome editing of the pluripotent stem cells, including embryonic stem cells (ESCs) and induced pluripotent stem cells (iPSCs), offers a great potential for modelling human genetic diseases as they can be differentiated into any tissue affected by the pathology. In the present invention, the cND-based approach can be utilized to safely and efficiently deliver CRISPR-Cas9 components to human iPSCs. By using our cND-mC-C/C9 delivery system, we could successfully introduce XLRS-specific mutation of RS1 gene (c.625C>T) into normal human iPSCs. In the future, such knock-in iPSCs can be used to study the molecular and cellular mechanisms of retinopathy by differentiating them into 3D retinal organoids and using parental iPSCs as a control with the same genetic background.

XLRS is the X-linked retinopathy caused by mutations in RS1 gene and characterized by splitting of the retinal layers. In previously characterized Rs1-knockout mouse model, several pathological features were demonstrated, including outer nuclear layer (ONL) thickness reduction and inner retinal cavitation. In the present invention, OCT imaging of mouse retinas treated with cND-mC-C/C9 nanoparticles did not reveal the presence of cysts in the retina, however, we clearly observed the merger of hyperreflective outer retinal bands 2 and 3, indicative of aberrant photoreceptor structure. Consistently, the analysis of retinal tissue sections revealed reduction of thickness of outer retinal layer and shortened morphology of photoreceptor cells. A partial human mutant Rs1 gene in adult male mice were prepared to show a phenotype of changes in the outer segment of the photoreceptor cells, which supports the idea that Rs1 gene inactivation may directly cause photoreceptor damage. Whereas intravitreal injection leads to exposure of all retinal cell types to the NDs, only the morphology of the photoreceptor layer was affected by it, thus corroborating the functional specificity of RS1 protein as the crucial factor for organization of the outer retina. On the other hand, the specificity of our ND-based vector to target the specific cell type, like photoreceptors, can potentially be increased by using the advantages of the design of this vector. As we used the COOH groups of the carboxylated NDs to covalently attach the mCherry reporter marker via the peptide bond, the cell-type specific ligand proteins can be concomitantly conjugated to target the NDs to the photoreceptor-specific surface markers.

Whereas the disadvantage of the ND-based vectors in comparison with the virus-based systems is their low transfection efficiency, their advantage is based on the higher safety as an inert and low immunogenicity material. By using scanning laser ophthalmoscopy, we observed that GFP signal persisted in the mouse retina for up to 12 days after the intravitreal injection of the NDs (FIG. 3A). Therefore, given higher safety of the NDs, we can speculate that the efficiency of in vivo genome editing can be increased by constantly maintaining high concentration of the NDs by injecting them once GFP signal is diminished.

The present invention is further illustrated by the following examples, which are provided for the purpose of demonstration rather than limitation.

EXAMPLE 1.1. CRISPR-Cas9 Design

The Cas9-GFP expression vector was described in a previous study [31]. The human RS1 c.625 C>T (p.R209C) mutation was introduced using the following sgRNA scaffold sequence:

(SEQ ID NO: 1)
GGCACGTCTGCATTGCCATCGTTTTAGAGCTAGAAATAGCAAGTTAAAAT

AAGGCTAGTCCGTTATCAACTTGAAAAAGTGGCACCGAGTCGGTGC;

and the following HDR sequence:

(SEQ ID NO: 2)
GTCTTCTATGGCAACTCGGACCGCACCTCCACGGTTCAGAACCTGCTGCG

GCCCCCCATCATCTCCCGCTTCATCCGCCTCATCCCGCTGGGCTGGCATG

TCCGGATTGCCATCCGGATGGAGCTGCTGGAGTGCGTCAGCAAGTGTGCC

TGATGCCTGCCTCAGCTCGGCGCCTGCCAGGGGGTGACTG.

The mouse Rs1 c.625 C>T was introduced using sgRNA scaffold sequence:

(SEQ ID NO: 3)
GGCATGTCCGAATTGCCATCGTTTTAGAGCTAGAAATAGCAAGTTAAAAT

AAGGCTAGTCCGTTATCAACTTGAAAAAGTGGCACCGAGTCGGTGC;

and HDR sequence:

(SEQ ID NO: 4)
GTCTTCTATGGAAACTCAGACCGGAGTTCTACAGTTCAGAACTTACTCAG

GCCCCCCATCATTTCCCGCTTCATCCGACTGATCCCTCTAGGCTGGCACG

TCtGtATTGCCATCCGGATGGAGCTGCTTGAGTGTGCCAGCAAGTGTGCC

TGATGTCTATTTCAGCTCAGTTCTGTCACTTGCAGGGAGA.

The sgRNA scaffold and HDR sequences were cloned into pUC57 vector (Addgene).

1.2. Preparation of Carboxylated Nanodiamond (cND) and Linkage with mCherry and Linear DNA The detonation nanodiamonds (NDs) were purchased from NanoCarbon Institute Co., Ltd in the form of 2.5% (w/v) water colloidal solution. According to the specifications of the supplied colloidal solution, it contains particles of the size distribution around 3.2 ±0.6 nm. Formation of graphene on ND surface and the minute contamination from zirconia beads and metal ions from the detonation chamber are present, but of little or no harm to this research. In order to functionalize the surface of NDs with carboxyl (COOH) group, they were treated with 3:1 mixture of H2SO4 and HNO3 with stirring at 100° C. for 72 h. The resultant carboxylated NDs (cNDs) were washed several timed in double-distilled water and suspended in PBS at a concentration of 250 µg/ml. mCherry protein was linked to cNDs by peptide with 1-ethyl-3-(3-dimethylaminopropyl)carbodiimide (EDC) used as a catalytic agent. cNDs (250 µg/ml suspension in PBS), mCherry protein (250 µg/ml), and 0.1 M ECD were mixed at a volume ratio of 1:2:3 and incubated on a rolling shaker at 4° C. for 18 h. The reaction products (cND-mCherry) were purified by dialysis against PBS for another 18 h. mCherry and linear DNA were linked by phosphoryl imidazole bond between imidazole group from mCherry 6His-tag tail and DNA phosphate group. cND-mCherry PBS solution (about 40 µg/ml), linearized DNA constructs (200 µg/ml) and 0.1 M ECD were mixed at a volume ratio of 5:2:1 and incubated on a rolling shaker at 4° C. for 18 h. The reaction products were purified by dialysis against PBS for another 18 h. Prior to applying the loaded NDs to the cells, bovine serum albumine (BSA) was added to a final concentration of 1 or 3% (w/v), and nanoparticles were sonicated for 2 h to prevent their aggregation and ensure even dispensing.

1.3. Transmission Electron Microscopy (TEM) and Fourier Transform Infrared Spectroscopy (FTIR)

TEM images of the NDs were obtained on a JEM-2000EX II (JEOL) run at 100 kV. NDs (40 µg/mL) were suspended in PBS and then pipetted onto a copper TEM grid (Ted Pella Inc.) and the solvent was removed after overnight deposition. Surface modification of ND was detected by FTIR using FT/IR-4200 spectrometer (JASCO) with a scan size (resolution) of 4 cm-1 and 256 scans per sample.

1.4. Human iPSCs

Human iPSCs were generated by reprogramming from peripheral blood mononuclear cells (PBMCs) of a healthy male Han Chinese donor as previously described [32].

Briefly, PBMCs were seeded into 24-well plates (5×10⁵ cells/well) in complete PBMC medium. PBMCs were transduced with a mix of SeV vectors encoding OCT3/4, SOX2, KLF4 and cMYC at a multiplicity of infection (MOI) of 3. The medium was changed every second day, and on day 7 post transduction, 1.25×10⁵ cells were plated onto a 10-cm dish precoated with a mouse embryonic fibroblast (MEF) feeder layer. On the next day, the medium was changed to hES medium and the cells were fed every other day for 7 days before switching to the daily feeding. Once the colonies emerged, they were mechanically dislodged and transferred to a fresh feeder. hiPSCs were cultured on Geltrex-coated cell culture dishes and incubated with mTeSR1 medium (STEMCELL Technologies). The cells were cultured in a 37° C. incubator containing 10% $CO_2$. The cells were cultured in a 37° C. incubator containing 10% CO 2. The hiPSCs cell line was characterized by typical iPSC morphology and positive alkaline phosphatase activity, expression of typical pluripotency markers as confirmed by RT-PCR and western blotting.

1.5. Cell viability assay

The iPSCs were seeded in 96-well plates at 5×10⁴ cells per well. After 24 h incubation, different doses of cND-mC-C/C9 mixed with BSA were added and incubated for 2 days. 10 μl of Cell Counting Assay Kit-8 solution (CCK-8, Sigma) was added to each well and incubated for 2 h. The absorbance at 490 nm was measured on a microplate reader. Cells treated with 10 μl of StemFlex medium (Thermo Fisher Scientific) instead of CCK-8 solution were used as a negative control. All experiments were performed independently three times.

1.6. Animals

C57BL/6 male mice (6~10 weeks old) were purchased from National Laboratory Animal Center (Taipei, Taiwan). The mice were housed in a pathogen-free space and operated according to the National Research Council's Guide for the Care and Use of Laboratory Animals. All anesthesia and sacrifice procedures were reviewed and approved by the Animal Care and Use Committee of the Taipei Veterans General Hospital (TVGH). The mice were anesthetized with 250 mg/kg tribromoethanol (Sigma-Aldrich) by intraperitoneal injection, and placed under a dissecting microscope (SZX16, OLYMPUS, Japan) or spectral-domain OCT imaging system.

1.7. Intravitreal Injection

Each mouse was intravitreally injected with 5 μl of different ND formulations into both eyes. The mix of NDs loaded with Cas9-GFP (15 ng/μl ) and Rs1-sgRNA (30 ng/μl) constructs was administered unilaterally, and NDs loaded with Cas9-GFP (15 ng/ul) were administered to the contralateral eye as a control. A Hamilton syringe was used to inject 5 μl of the NDs into the vitreous cavity of an eye through the sclera behind the limbus of mice. During the procedure, about 5 μl of vitreous liquid was allowed to efflux through the puncture hole to allow the complete delivery of 5 μl of ND formulation.

1.8. Spectral Domain OCT Imaging

The OCT images of the mouse retinas were obtained using a continuous, high-speed and high-resolution retinal image acquisition system (axial resolution, 7 μm; acquisition speed, 76 frames/s, 1000×1024 pixels in the X-Z plane) as previously described [33]. A horizontal scan of 400 images was obtained through the fundus.

1.9. Droplet Digital PCR (ddPCR)

The genomic DNA copy number was quantified by ddPCR (BioRad). All primers and probe sequences (Suppl. Table 1) were designed on the OligoAnalyzer software (IDT). The ddPCR Supermix (no dUTP) for the probe was used in the droplets.

1.10. Statistical Analysis

Unpaired Student's t-test was applied to assess numerical data statistical significance. Statistical significance was set at p-value less than 0.05. The calculations were performed using Excel software.

2. Results 2.1 The Design of CRISPR-Cas9 Constructs to Introduce RS1 Mutation and Functionalization of mCherry-Labeled NDs for their Delivery In this study, we aimed to develop the approach of using NDs to create the disease model of XLRS by adapting them as a vehicle for the delivery of CRISPR-Cas9 genome editing system in order to modify XLRS-associated RS1 gene. The RS1 mutation c.625>T, leading to amino acid substitution p.R209C, is one of the known causative mutations in XLRS. The patient carrying this mutation (FIG. 1A) was characterized by typical features of XLRS, such as clearly developed bilateral macular atrophy in the retina observed by ophthalmoscopy (FIG. 1B), and typical schisis phenotype observed by optical coherence tomography (OCT) in both eyes (FIG. 1C). To express the components of CRISPR-Cas9 editing system, two linear DNA constructs were designed. RS1-sgRNA construct contained a homology directed repair (HDR) template and encoded sgRNA directing the c.625>T mutation in exon 6 of RS1 gene (FIG. 2A). Cas9-GFP construct encoded Cas9 endonuclease and GFP reporter (FIG. 2A).

Figure 2B:
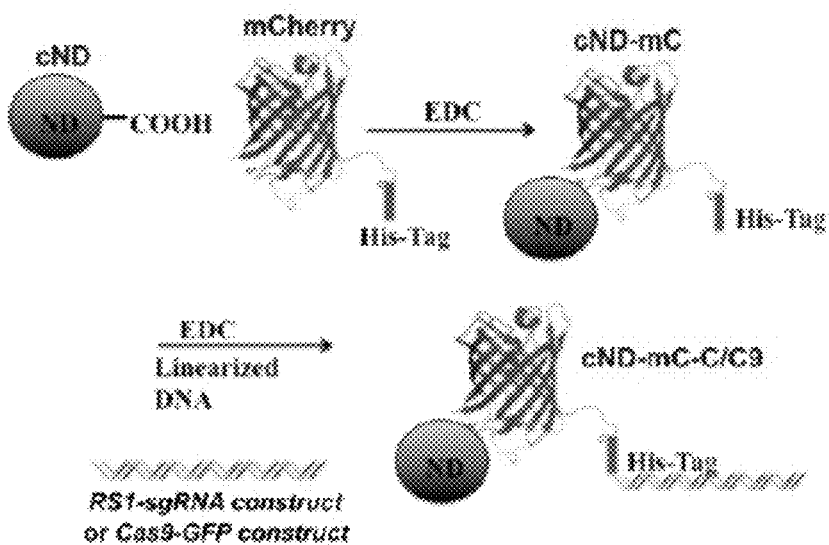
FIG. 2B provides the scheme showing the design and production of CRISPR-Cas9-loaded NDs, wherein the carboxylated NDs (cNDs) were covalently linked to mCherry via COOH group in a reaction catalyzed by EDC to produce cND-mC, Cas9-GFP and RS1-sgRNA linear DNA was linked to cND-mC via His-tag to produce cND-mC-C/C9.
Figure 2C:
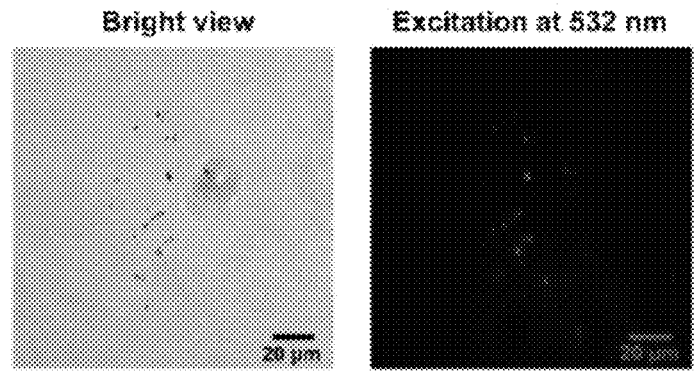
FIG. 2C provides a bright view and fluorescence microscopy image of cNDs coupled to mCherry.
Figure 2D:
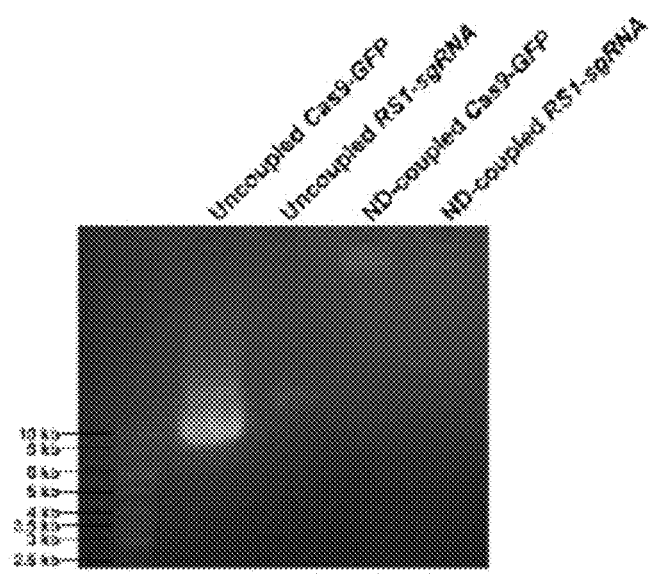
FIG. 2D shows agarose gel showing migration of uncoupled and ND-coupled Cas9-GFP and RS1-sgRNA DNA constructs.
Figure 2E:
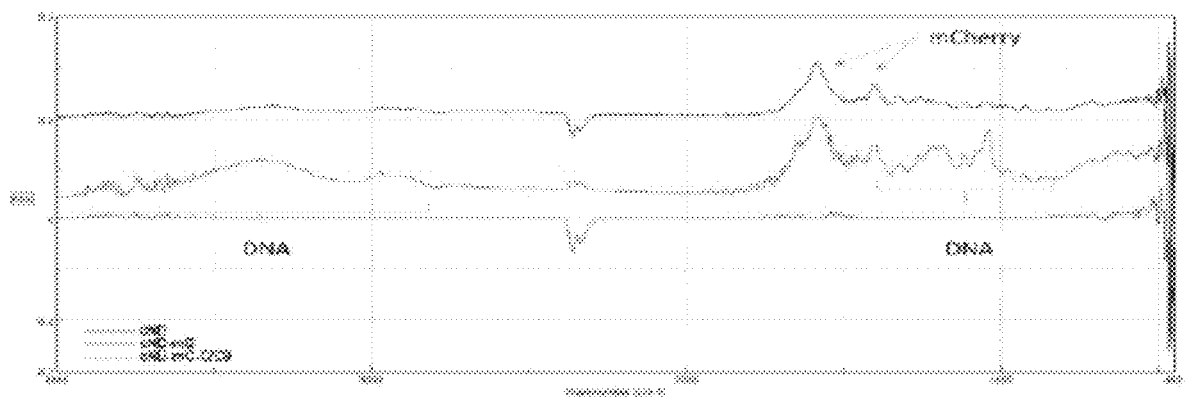
-FIG. 2E shows the design of CRISPR-Cas9 constructs to introduce RS1 mutation and functionalization of mCherry-labeled NDs for their delivery.
Figure 2F:
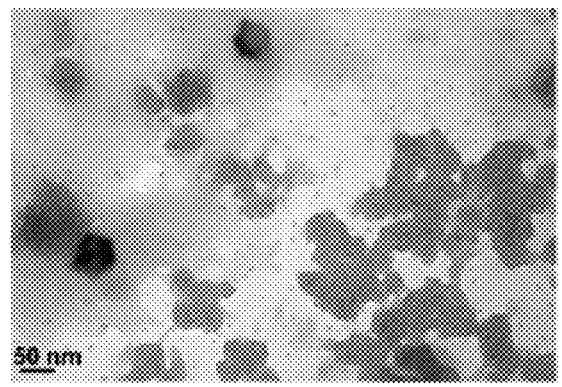
FIG. 2F provides TEM image of BSA-mixed cND-mC-C/C9 nanoparticles.

The original NDs were obtained by detonation method and their diameter was 3 nm. In order to attach the cargo, the surface of the NDs was functionalized by introducing the carboxyl groups using a strong oxidizing acid. The carboxylated NDs (cND) were then covalently linked with mCherry protein via the carboxyl groups, thus allowing fluorescent detection of these particles (cND-mC) (FIG. 2B and FIG. 2C). mCherry protein was designed to carry a polyhistidine tail to be used for covalent attachment of the 5'-phosphate group of linear DNA, encoding components of CRISPR-Cas9 editing system (FIG. 2B). By agarose gel electrophoresis analysis, we showed that DNA was bound to the cND-mC particles (FIG. 2D). By comparing the Fourier-transform infrared (FTIR) spectra of cND, cND-mC, and cND-mC-C/C9 nanoparticles, we found that the distinctive FTIR peak at 1640 $cm^{-1}$ was observed in the latter two types, indicating the presence of mCherry protein (FIG. 2E). At the same time, the peaks indicating the presence of DNA moiety were observed in the FTIR spectrum of cND-mC-C/C9 nanoparticles (FIG. 2D). The resultant NDs carrying mCherry and CRISPR-Cas9-encoding linear DNA (cND-mC-C/C9) were mixed with bovine serum albumin (BSA) to facilitate their delivery to cells and were observed by transmission electron microscopy (TEM), their average size, as determined by ImageJ, was 5.6+/−0.99 nm (FIG. 2F).

2.2 Editing of RS1 Gene by cND-mC-C/C9 in hiPSCs

As our initial objective, we aimed to use cND-mC-C/C9 nanoparticles to introduce the XLRS-associated RS1 mutation in human induced pluripotent stem cells (hiPSCs). Previous studies have shown that BSA stabilizes fluorescence brightness and prevents NDs from aggregation in phosphate buffer [34, 35]. Therefore, we treated hiPSC culture with cND-mC-C/C9 particles diluted in PBS with different concentrations of BSA (0%, 1% and 3%). To evaluate whether cND-mC-C/C9 nanoparticles were internalized by hiPSCs, the expression of fluorescent markers was observed under a fluorescent microscope. The fluorescence signals from both mCherry and GFP were observed inside the cells signifying that cND-mC-C/C9 particles were both internalized and the attached DNA was transcribed (FIG. 3A). The average size of mCherry fluorescent dots was significantly smaller inside the cells treated with 3% BSA cND-mC-C/C9, indicating that mixing with BSA prevented particle aggregation (FIG. 3B). Moreover, cND-mC-C/C9 mixed with 3% BSA were more efficiently delivered to the cells as compared to nanoparticles without BSA and mixed with 1% BSA (FIG. 3C). Two days after the treatment of hiPSCs with cND-mC-C/C9 mixed with 3% BSA, GFP-expressing cells were sorted by flow cytometry. The RS1 c.625>T gene mutation in genomic DNA was analyzed by droplet digital PCR (ddPCR), and it was shown that this nucleotide was edited in ~19.3% of all alleles (FIG. 3D). To test whether cND-mC-C/C9 have any toxic effects, hiPSCs were treated with different concentrations of 3% BSA-mixed cND-mC-C/C9 nanoparticles for two days, and their viability was assessed by CCK-8 assay. It was shown that in a range of concentrations between 1.5 and 24 µg/ml, cND-mC-C/C9 did not affect the viability of hiPSCs (FIG. 3E). To summarize, these results indicate that the BSA-mixed cND-mC-C/C9 nanoparticles can be delivered to the hiPSCs, successfully edit their genome, and don't affect their viability.

2.3 cND-mC-C/C9 Delivery into the Mouse Retina

Figure 4A:
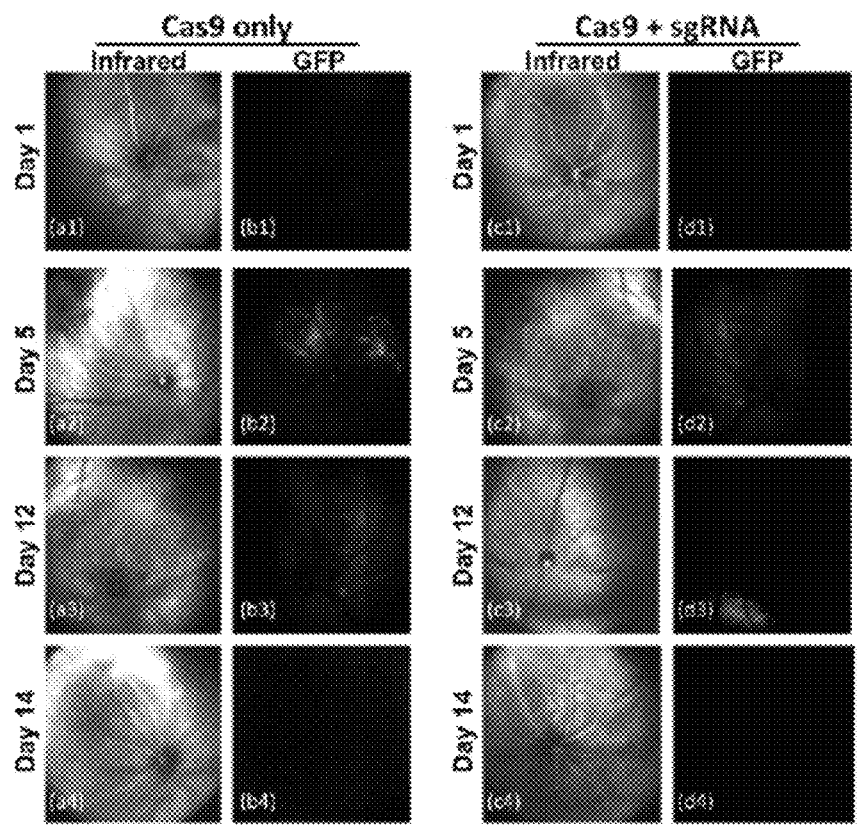
FIG. 4A-FIG. 4D show the cND-mC-C/C9 delivery into the mouse retina.
Figure 4B:
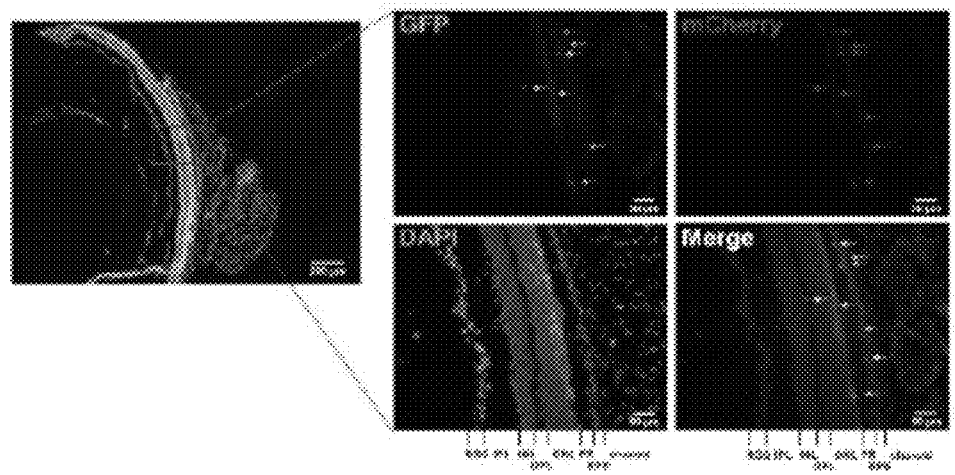
Figure 4C:
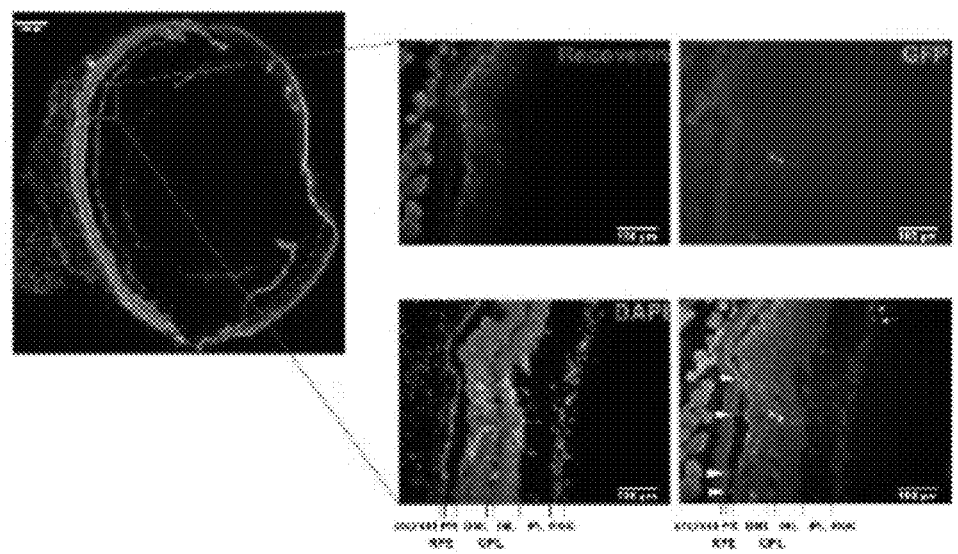
Figure 4D:
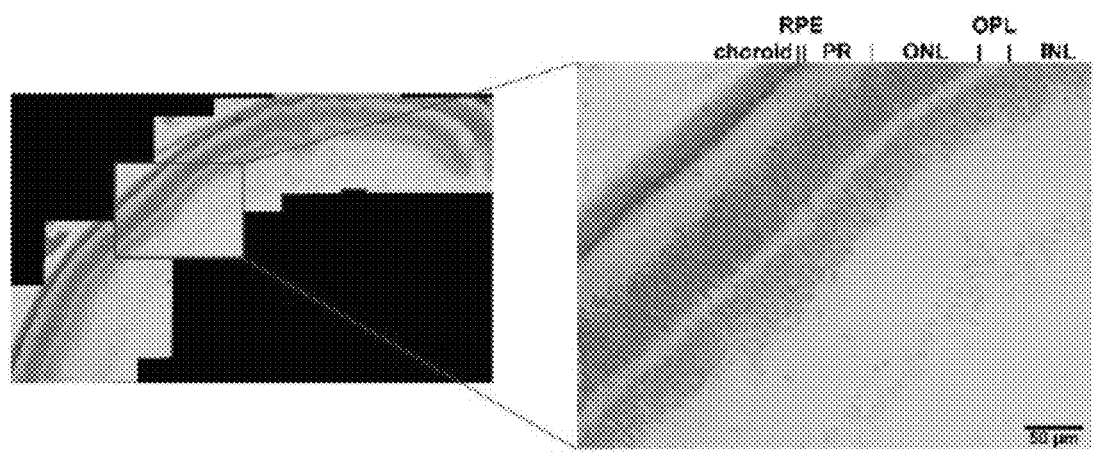

To study the effects of cND-mC-C/C9 in vivo, we examined the distribution of nanoparticles in the mouse retina after cND-mC-C/C9 infusion. cND-mC-C/C9 particles mixed with 3% BSA were injected into the mouse eye by intravitreal injection and examined by scanning laser ophthalmoscopy (SLO) in live animals in a time course of two weeks. The fluorescence signals of GFP was clearly observed in the fundus of the retina, indicating to cND-mC-C/C9 internalization and expression (FIG. 4A). Confocal microscopy of transverse retinal sections showed the presence of mCherry signals and GFP expression in different retinal layers, including photoreceptor (PR), outer nuclear layer (ONL), inner nuclear layer (INL), and retinal ganglion cell (RGC) layer (FIG. 4B and FIG. 4C). In addition, H&E staining of transverse retinal sections showed that cND-mC-C/C9 infusion did not affect retinal structure (FIG. 4D). These findings suggest that cND-mC-C/C9 mixed with BSA represent a safe and effective retinal delivery system.

2.4 Editing of Rs1 Gene by cND-mC-C/C9 in the Mouse Retina

Figure 5A:
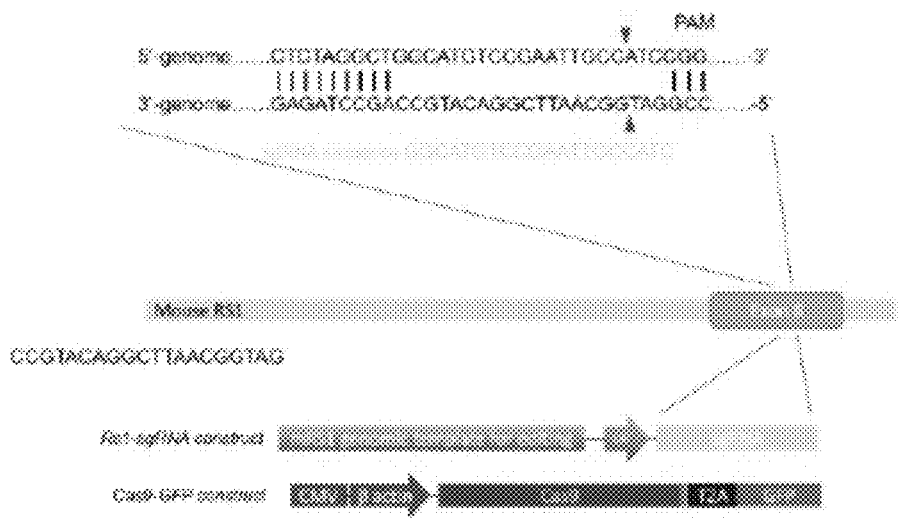
FIG. 5A-FIG. 5D show the editing of Rs1 gene by cND-mC-C/C9 in the mouse retina.
Figure 5B:
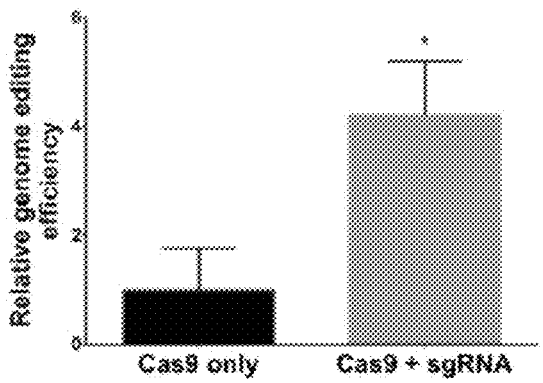
Figure 5C:
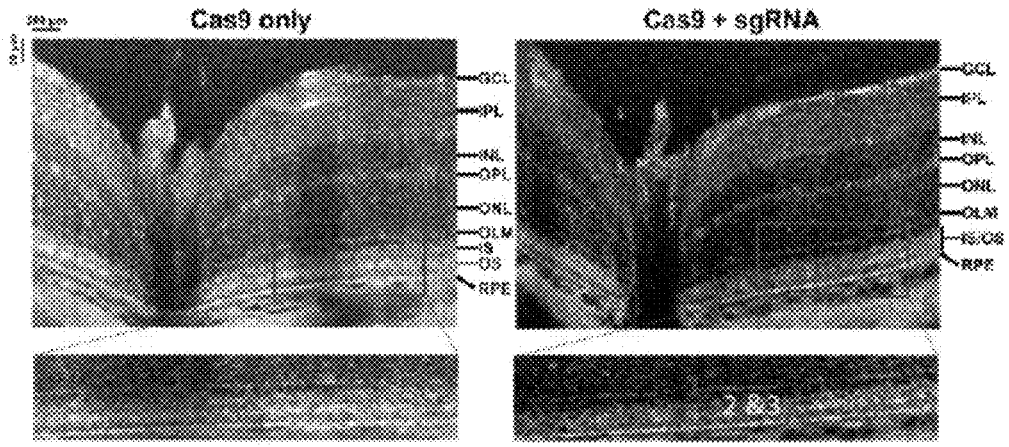
Figure 5D:
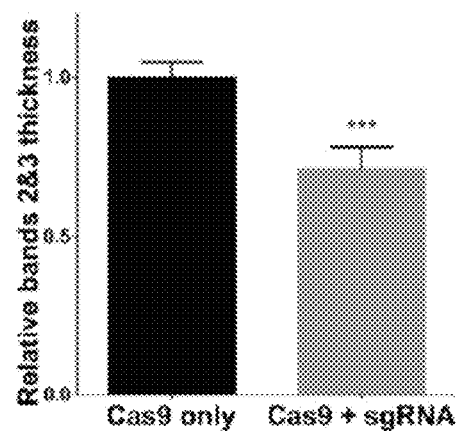
Figure 5E:
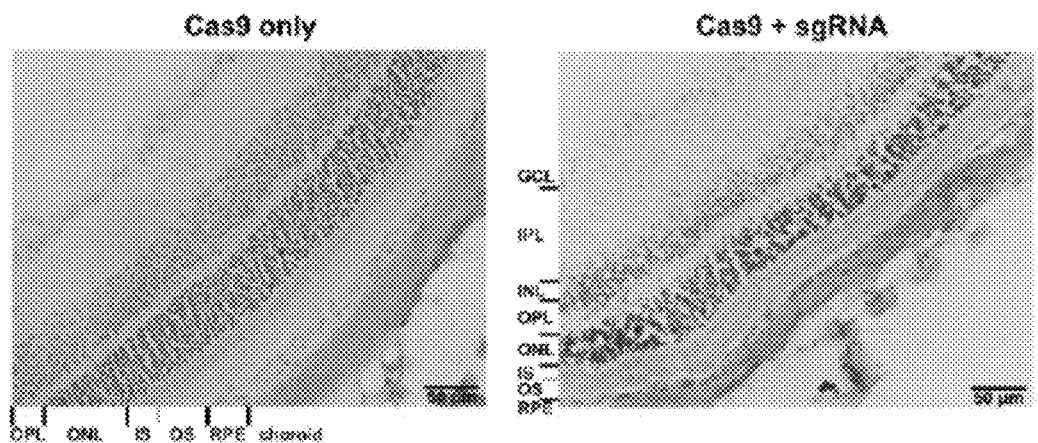
FIG. 5E provides the H&E staining of cross sections of mouse retinas treated for two weeks with control (Cas9 only) and (Cas9+sgRNA) cND-mC-C/C9 nanoparticles.
Figure 5F:
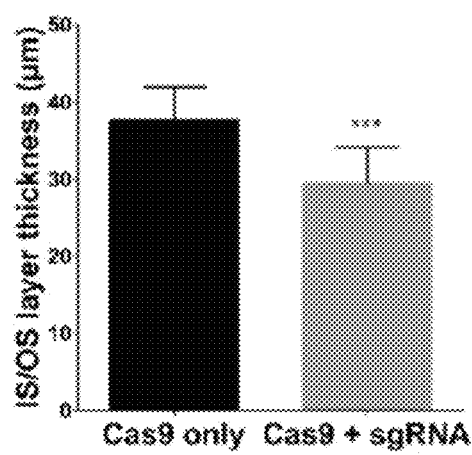
FIG. 5F shows the quantification of thickness of IS/OS layer in OCT images in FIG. 5E. The data expressed as means from 3 measurements, "Cas9+sgRNA" quantified relative to "Cas9 only" control.

We sought to investigate the efficiency and functional effects of genome editing by cND-mC-C/C9 nanoparticles in the mouse retina. Two linear DNA constructs, Rs1-sgRNA, encoding sgRNA and containing HDR template insert, as well as Cas9-GFP, encoding Cas9 endonuclease and GFP reporter, were designed to introduce c.625C>T mutation into the murine Rs1 gene (FIG. 5A). These constructs were attached to cND-mC nanoparticles to produce cND-mC-C/C9, which in turn were injected into the mouse eyes. Two weeks after the injection, the percentage of edited alleles in retinal lysates was assessed by ddPCR, and was found to be about four times higher than the background signal detected in the retina of mice injected with cND-mC-C/C9 particles carrying Cas9-GFP construct only (FIG. 5B). The fine anatomical structure of these retinas was observed by high-resolution OCT [36]. Whereas the retinas treated with cND-mC-C/C9 carrying Cas9-GFP construct only displayed the normally organized lamellar structure, the retinas treated with both constructs were characterized by highly undefined border between hyperreflective outer retinal bands 2 and 3, corresponding to ellipsoid region of photoreceptor inner segment (IS) and phagosome region of photoreceptor outer segment (OS), respectively (FIG. 5C). The thickness of the combined hyperreflective outer retinal bands 2 and 3 was significantly reduced in Cas9+sgRNA treated retinas by approximately 30% (FIG. 5D). Similarly, the H&E staining of the histology sections also revealed thickness reduction of IS/OS layer (FIG. 5E and FIG. 5F). In addition, the histology section showed loose outer nuclear layer (ONL) and inner nuclear layer (INL) structure, which was not evident from OCT images (FIG. 5E). Taken together, our findings indicate that cND-mC-C/C9 treatment causes disruption in organization of photoreceptor layers (ONL, IS, and OS).

Figure 6A:
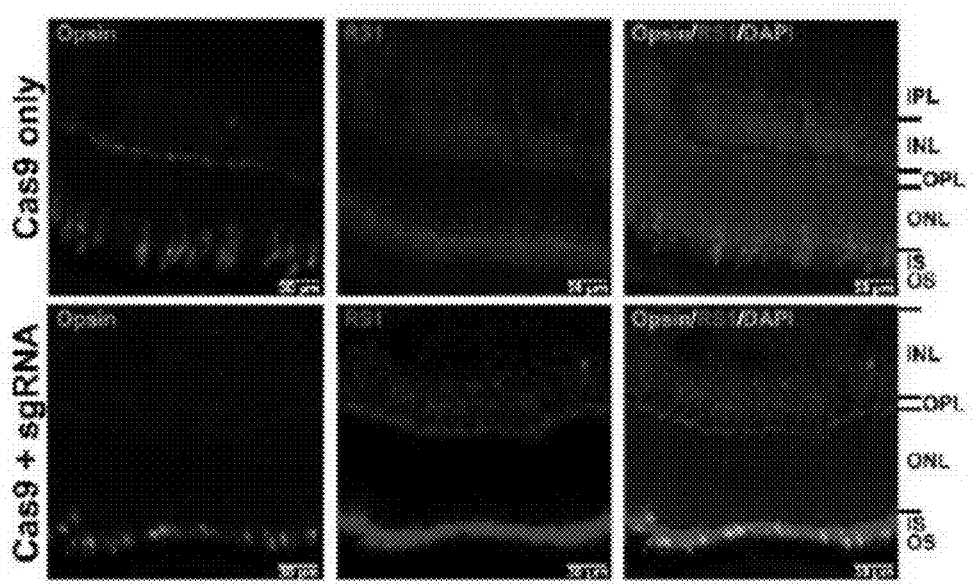
FIG. 6A-FIG. 6C show the effect of cND-mC-C/C9-mediated Rs1 editing on photoreceptor cells in the mouse retina. Immunofluorescence staining of the cross sections of the mouse retinas treated with the control cND-mC-C/C9 particles (Cas9 only) and cND-mC-C/C9 particles targeting Rs1 gene (Cas9+sgRNA). The layers of the retina indicated on the right: IPL—inner plexiform layer, INL—inner nuclear layer, OPL—outer plexiform layer, ONL—outer nuclear layer, IS—inner segments, OS—outer segments. Nuclei labeled with DAPI.
Figure 6B:
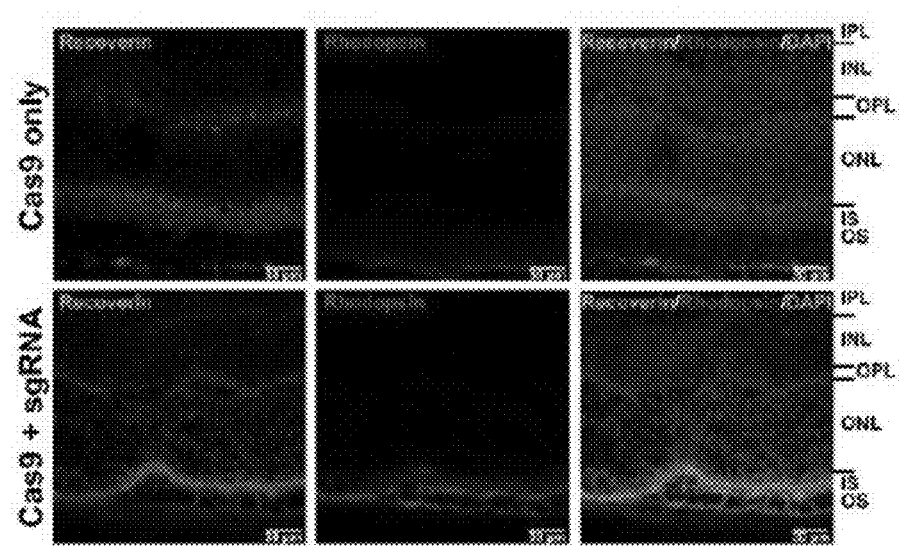
Figure 6C:
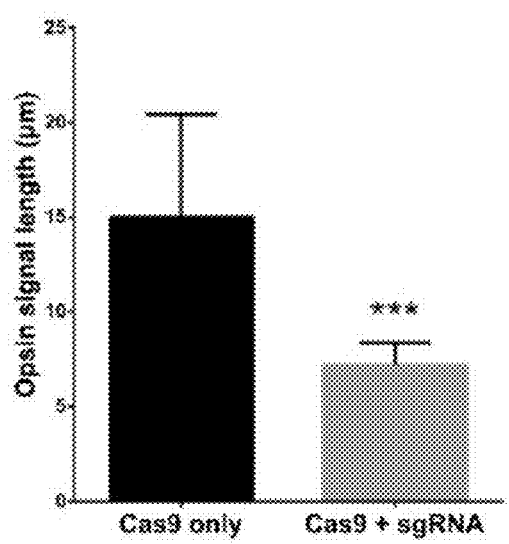

2.5 Effect of cND-mC-C/C9-Mediated Rs1 Editing on Photoreceptor Cells in the Mouse Retina To further study the effect of cND-mediated Rs1 gene editing on photoreceptors, we immunostained photoreceptor markers such as rhodopsin, cone cell-specific opsins, recoverin, and RS1 in the cross section of the mouse retinas. RS1 protein is normally expressed in photoreceptors and bipolar cells of the mouse retina [13]. Here, we observed that in the control retinas (treated with cND-mC-C/C9 carrying Cas9-GFP only), RS1 protein was enriched in the inner segment (IS) layer of the photoreceptors, but its localization was also extended to the outer nuclear layer (ONL), outer plexiform layer (OPL), and inner nuclear layer (INL) (FIG. 6A, middle). On the other hand, the retinas treated with cND-mC-C/C9 particles carrying both CRISPR-Cas9 constructs were characterized by more concentrated localization in the IS layer and less spread to the other layers (FIG. 6A, middle). Cone cell-specific opsins are normally localized in the outer segments of the cone cells and appear as linear and parallel signals in immunofluorescence staining imaging [37]. Indeed, such pattern of localization of cone cell-specific opsins was observed in the retinas treated with the control cND-mC-C/C9 (Cas9 only). On the contrary, retinas treated with Rs1-targeting cND-mC-C/C9 were characterized by significantly shorter and point-like appearance of opsin signal (FIG. 6A and FIG. 6C). Recoverin protein is known to be expressed in rod, cone, and bipolar cells, while rhodopsin is considered to be a marker of rod cells [38-40]. The results of immunofluorescence staining showed that recoverin had significant immunoreactivity in the OPL, ONL, IS and OS of the control mouse retina (FIG. 6B, left). In addition, rhodopsin had strong immunoreactivity in OS (FIG. 6B, middle). The injection of Rs1-targeting cND-mC-C/C9 (Cas9+sgRNA) clearly caused more disordered localization of recoverin and rhodopsin in the IS/OS region, and in addition, the presence of the recoverin protein in the OPL was also irregular (FIG. 6B, left).

Figure 7:
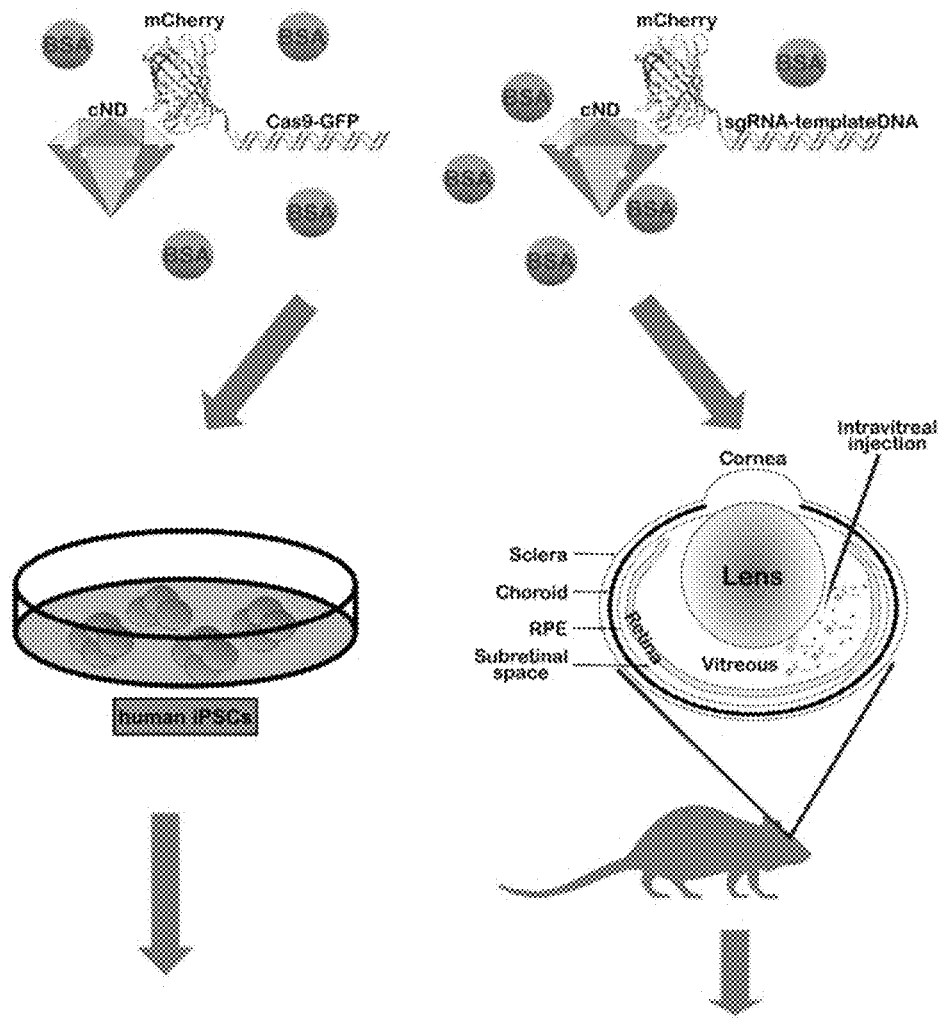
FIG. 7 shows the summary of the study, wherein the nanodiamonds were functionalized to covalently attach mCherry protein and DNA constructs encoding components of CRISPR-Cas9 genome editing system. Nanoparticles were mixed with BSA and used to edit the genomes of iPSCs and mouse retinas, thus making them a useful tool to create the in vitro and in vivo disease models, respectively.

In conclusion, the ND-based delivery system was designed to deliver the CRISPR-Cas9 components into human iPSCs and mouse retina. For this purpose, NDs were functionalized by adding carboxyl groups, which were used to attach mCherry protein and covalently link linear DNA encoding components of CRISPR-Cas9 system, including HDR template, sgRNA, Cas9 protein and GFP reporter. These NDs could be internalized by iPSCs and mouse retinas, and could introduce XLRS-specific mutation of RS1 gene. Mixing of NDs with BSA significantly increased the uptake by the cells. We demonstrated that the treatment of mouse retinas with CRISPR-Cas9-loaded NDs caused defects in organization of photoreceptor cells, which is a typical feature of XLRS. Therefore, we believe our ND-based strategy of genome editing has a great potential for establishing in vitro and in vivo disease models of XLRS (FIG. 7).

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment.

REFERENCES

[1] S. K. Sikkink, S. Biswas, N. R. Parry, P. E. Stanga, D. Trump, X-linked retinoschisis: an update, J Med Genet 44(4) (2007) 225-32.
[2] R. S. Molday, U. Kellner, B. H. Weber, X-linked juvenile retinoschisis: clinical diagnosis, genetic analysis, and molecular mechanisms, Prog Retin Eye Res 31(3) (2012) 195-212.
[3] A. Tantri, T. R. Vrabec, A. Cu-Unjieng, A. Frost, W. H. Annesley, Jr., L. A. Donoso, X-linked retinoschisis: a clinical and molecular genetic review, Sury Ophthalmol 49(2) (2004) 214-30.
[4] C. G. Sauer, A. Gehrig, R. Warneke-Wittstock, A. Marquardt, C. C. Ewing, A. Gibson, B. Lorenz, B. Jurklies, B. H. Weber, Positional cloning of the gene associated with X-linked juvenile retinoschisis, Nature genetics 17(2) (1997) 164-70.
[5] W. W. Wu, R. S. Molday, Defective discoidin domain structure, subunit assembly, and endoplasmic reticulum processing of retinoschisin are primary mechanisms responsible for X-linked retinoschisis, J Biol Chem 278(30) (2003) 28139-46.
[6] C. A. Curat, M. Eck, X. Dervillez, W. F. Vogel, Mapping of epitopes in discoidin domain receptor 1 critical for collagen binding, J Biol Chem 276(49) (2001) 45952-8.
[7] W. Vogel, Discoidin domain receptors: structural relations and functional implications, FASEB journal: official publication of the Federation of American Societies for Experimental Biology 13 Suppl (1999) S77-82.
[8] L. C. Eksandh, V. Ponjavic, R. Ayyagari, E. L. Bingham, K. T. Hiriyanna, S. Andreasson, B. Ehinger, P. A. Sieving, Phenotypic expression of juvenile X-linked retinoschisis in Swedish families with different mutations in the XLRS1 gene, Archives of ophthalmology (Chicago, Ill.: 1960) 118(8) (2000) 1098-104.
[9] Y. Inoue, S. Yamamoto, M. Okada, M. Tsujikawa, T. Inoue, A. A. Okada, S. Kusaka, Y. Saito, K. Wakabayashi, Y. Miyake, T. Fujikado, Y. Tano, X-linked retinoschisis with point mutations in the XLRS1 gene, Archives of ophthalmology (Chicago, Ill.: 1960) 118(1) (2000) 93-6.
[10] X. Li, X. Ma, Y. Tao, Clinical features of X linked juvenile retinoschisis in Chinese families associated with novel mutations in the RS1 gene, Molecular vision 13 (2007) 804-12.
[11] T. Wang, A. Zhou, C. T. Waters, E. O'Connor, R. J. Read, D. Trump, Molecular pathology of X linked retinoschisis: mutations interfere with retinoschisin secretion and oligomerisation, Br J Ophthalmol 90(1) (2006) 81-6.
[12] C. M. Mooy, L. I. Van Den Born, S. Baarsma, D. A. Paridaens, T. Kraaijenbrink, A. Bergen, B. H. Weber, Hereditary X-linked juvenile retinoschisis: a review of the role of Muller cells, Archives of ophthalmology (Chicago, Ill.: 1960) 120(7) (2002) 979-84.
[13] L. L. Molday, D. Hicks, C. G. Sauer, B. H. Weber, R. S. Molday, Expression of X-linked retinoschisis protein RS1 in photoreceptor and bipolar cells, Investigative ophthalmology & visual science 42(3) (2001) 816-25.
[14] S. N. Reid, C. Yamashita, D. B. Farber, Retinoschisin, a photoreceptor-secreted protein, and its interaction with bipolar and muller cells, The Journal of neuroscience: the official journal of the Society for Neuroscience 23(14) (2003) 6030-40.
[15] Z. Y. Lien, T. C. Hsu, K. K. Liu, W. S. Liao, K. C. Hwang, J. I. Chao, Cancer cell labeling and tracking using fluorescent and magnetic nanodiamond, Biomaterials 33(26) (2012) 6172-85.
[16] K. K. Liu, C. C. Wang, C. L. Cheng, J. I. Chao, Endocytic carboxylated nanodiamond for the labeling and tracking of cell division and differentiation in cancer and stem cells, Biomaterials 30(26) (2009) 4249-59.
[17] L. Moore, J. Yang, T. T. Lan, E. Osawa, D. K. Lee, W. D. Johnson, J. Xi, E. K. Chow, D. Ho, Biocompatibility Assessment of Detonation Nanodiamond in Non-Human Primates and Rats Using Histological, Hematologic, and Urine Analysis, ACS Nano 10(8) (2016) 7385-400.
[18] C. C. Fu, H. Y. Lee, K. Chen, T. S. Lim, H. Y. Wu, P. K. Lin, P. K. Wei, P. H. Tsao, H. C. Chang, W. Fann, Characterization and application of single fluorescent nanodiamonds as cellular biomarkers, Proceedings of the National Academy of Sciences of the United States of America 104(3) (2007) 727-32.
[19] X. Q. Zhang, M. Chen, R. Lam, X. Xu, E. Osawa, D. Ho, Polymer-functionalized nanodiamond platforms as vehicles for gene delivery, ACS Nano 3(9) (2009) 2609-16.
[20] H. L. Chu, H. W. Chen, S. H. Tseng, M. H. Hsu, L. P. Ho, F. H. Chou, M. P. Li, Y. C. Chang, P. H. Chen, L. Y. Tsai, C. C. Chou, J. S. Chen, T. M. Cheng, C. C. Chang, Development of a growth-hormone-conjugated nanodiamond complex for cancer therapy, ChemMedChem 9(5) (2014) 1023-9.
[21] C. Y. Cheng, E. Perevedentseva, J. S. Tu, P. H. Chung, C. L. Cheng, K. K. Liu, J. I. Chao, P. H. Chen, C. C. Chang, Direct and in vitro observation of growth hormone receptor molecules in A549 human lung epithelial cells by nanodiamond labeling, Applied Physics Letters 90(16) (2007).
[22] M. G. Chernysheva, I. Y. Myasnikov, G. A. Badun, Myramistin adsorption on detonation nanodiamonds in the development of drug delivery platforms, Diamond and Related Materials 55 (2015) 45-51.
[23] V. N. Mochalin, A. Pentecost, X. M. Li, I. Neitzel, M. Nelson, C. Wei, T. He, F. Guo, Y. Gogotsi, Adsorption of drugs on nanodiamond: toward development of a drug delivery platform, Mol Pharm 10(10) (2013) 3728-35.
[24] K. Turcheniuk, V. N. Mochalin, Biomedical applications of nanodiamond (Review), Nanotechnology 28(25) (2017) 252001.
[25] H. S. Choi, W. Liu, P. Misra, E. Tanaka, J. P. Zimmer, B. Itty Ipe, M. G. Bawendi, J. V. Frangioni, Renal clearance of quantum dots, Nat Biotechnol 25(10) (2007) 1165-70.
[26] Z. U. Hasan, P. R. Hemmer, H. Lee, A. L. Migdall, O. Shenderova, N. Nunn, T. Oeckinghaus, M. Torelli, G. McGuire, K. Smith, E. Danilov, R. Reuter, J. Wrachtrup, A. Shames, D. Filonova, A. Kinev, Commercial quantities of ultrasmall fluorescent nanodiamonds containing color centers, Advances in Photonics of Quantum Computing, Memory, and Communication X, 2017.
[27] F. C. Barone, C. Marcinkiewicz, J. Li, M. Sternberg, P. I. Lelkes, D. A. Dikin, P. J. Bergold, J. A. Gerstenhaber, G. Feuerstein, Pilot study on biocompatibility of fluorescent nanodiamond-(NV)-Z-800 particles in rats: safety, pharmacokinetics, and bio-distribution (part III), Int J Nanomedicine 13 (2018) 5449-5468.
[28] K. Purtov, A. Petunin, E. Inzhevatkin, A. Burov, N. Ronzhin, A. Puzyr, V. Bondar, Biodistribution of Different Sized Nanodiamonds in Mice, Journal of Nanoscience and Nanotechnology 15(2) (2015) 1070-1075.
[29] E. Perevedentseva, Y. C. Lin, M. Jani, C. L. Cheng, Biomedical applications of nanodiamonds in imaging and therapy, Nanomedicine (Lond) 8(12) (2013) 2041-60.
[30] M. Yu, J. Zheng, Clearance Pathways and Tumor Targeting of Imaging Nanoparticles, ACS Nano 9(7) (2015) 6655-74.
[31] E. R. Burnight, M. Gupta, L. A. Wiley, K. R. Anfinson, A. Tran, R. Triboulet, J. M. Hoffmann, D. L. Klaahsen, J. L. Andorf, C. Jiao, E. H. Sohn, M. K. Adur, J. W. Ross, R. F. Mullins, G. Q. Daley, T. M. Schlaeger, E. M. Stone, B. A. Tucker, Using CRISPR-Cas9 to Generate Gene-Corrected Autologous iPSCs for the Treatment of Inherited Retinal Degeneration, Mol Ther 25(9) (2017) 1999-2013.
[32] J. H. Chuang, A. A. Yarmishyn, D. K. Hwang, C. C. Hsu, M. L. Wang, Y. P. Yang, K. H. Chien, S. H. Chiou, C. H. Peng, S. J. Chen, Expression profiling of cell-intrinsic regulators in the process of differentiation of human iPSCs into retinal lineages, Stem Cell Res Ther 9(1) (2018) 140.
[33] P. H. Chen, C. H. Wu, Y. F. Chen, Y. C. Yeh, B. H. Lin, K. W. Chang, P. Y. Lai, M. C. Hou, C. L. Lu, W. C. Kuo, Combination of structural and vascular optical coherence tomography for differentiating oral lesions of mice in different carcinogenesis stages, Biomed Opt Express 9(4) (2018) 1461-1476.
[34] Y. K. Tzeng, O. Faklaris, B. M. Chang, Y. Kuo, J. H. Hsu, H. C. Chang, Superresolution imaging of albumin-conjugated fluorescent nanodiamonds in cells by stimulated emission depletion, Angew Chem Int Ed Engl 50(10) (2011) 2262-5.
[35] K.-i. Hanaki, A. Momo, T. Oku, A. Komoto, S. Maenosono, Y. Yamaguchi, K. Yamamoto, Semiconductor quantum dot/albumin complex is a long-life and highly photostable endosome marker, Biochemical and Biophysical Research Communications 302(3) (2003) 496-501.
[36] J. P. Syu, W. Buddhakosai, S. J. Chen, C. C. Ke, S. H. Chiou, W. C. Kuo, Supercontinuum source-based multi-contrast optical coherence tomography for rat retina imaging, Biomed Opt Express 9(12) (2018) 6132-6144.
[37] Y. Liang, D. Fotiadis, T. Maeda, A. Maeda, A. Modzelewska, S. Filipek, D. A. Saperstein, A. Engel, K. Palczewski, Rhodopsin signaling and organization in heterozygote rhodopsin knockout mice, J Biol Chem 279(46) (2004) 48189-96.
[38] A. H. Milam, D. M. Dacey, A. M. Dizhoor, Recoverin immunoreactivity in mammalian cone bipolar cells, Visual neuroscience 10(1) (1993) 1-12.
[39] K. Sakurai, J. Chen, S. C. Khani, V. J. Kefalov, Regulation of mammalian cone phototransduction by recoverin and rhodopsin kinase, J Biol Chem 290(14) (2015) 9239-50.
[40] K. Szabo, A. Szabo, A. Enzsoly, A. Szel, A. Lukats, Immunocytochemical analysis of misplaced rhodopsin-positive cells in the developing rodent retina, Cell and tissue research 356(1) (2014) 49-63.

What is claimed is:

1. A delivery system for gene editing comprising nanodiamond (ND) particles as carriers of CRISPR-Cas9 components including a Cas9 protein, a guide RNA (gRNA), a template DNA designed to introduce a mutation in a given gene, wherein the ND particles each has a diameter less than 5 nm, and is functionalized by carboxylation of their surface and covalently conjugated with an mCherry protein comprising a polyhistidine tag;
   wherein the ND particles are a mixture of:
   (i) a first ND particle linked, through the polyhistidine tag by phosphoryl imidazole, with a first linear DNA construct for expression of the Cas9 protein, and
   (ii) a second ND particle linked, through the polyhistidine tag by phosphoryl imidazole, with a second linear DNA construct for expression of the gRNA/template DNA; and wherein the ND particles enter a cell and enter a cell nucleus of the cell.

2. The delivery system of claim 1, wherein the ND particles have a diameter in a range of 3 nm or more to less than 5 nm.

3. The delivery system of claim 1, wherein the ND particles have a diameter of about 3 nm.

4. The delivery system of claim 1, further comprising bovine serum albumin (BSA) mixed with the ND particles.

5. The delivery system of claim 1, wherein the given gene is RSI gene associated with X-linked retinoschisis (XLRS).

6. The delivery system of claim 1, wherein the first linear DNA construct encodes for Cas9 endonuclease and a green fluorescent protein (GFP) reporter.

7. The delivery system of claim 5, wherein the first linear DNA construct encodes for Cas9 endonuclease and a GFP reporter.

8. A method for treating a disease or repairing a tissue damage in a subject, comprising delivering and internalizing the mutation in a given gene into said subject through the delivery system of claim 1.

9. The method of claim 8, wherein the disease is X-linked retinoschisis (XLRS).

10. The method of claim 9, wherein the given gene is RSI gene associated with X-linked retinoschisis (XLRS).

11. A method for creating an in vitro or in vivo disease model, comprising delivering and internalizing the mutation in a given gene into induced pluripotent stem cells (iPSCs) or an animal organ through the delivery system of claim 1.

12. The method of claim 11, wherein the disease is X-linked retinoschisis (XLRS).

13. The method of claim 12, wherein the given gene is RS1 gene associated with X-linked retinoschisis (XLRS).

14. The method of claim 12, wherein the animal organ is mouse retinas.

15. The method of claim 14, wherein the RSI gene editing in the mouse retinas results in several pathological features typical for XLRS.

16. The method of claim 15, wherein the pathological feature typical for XLRS is aberrant photoreceptor structure.

\* \* \* \* \*

SEQUENCE LISTING

```
<160> NUMBER OF SEQ ID NOS: 13

<210> SEQ ID NO 1
<211> LENGTH: 96
<212> TYPE: DNA
<213> ORGANISM: Artificial Sequence
<220> FEATURE:
<223> OTHER INFORMATION: Synthetic

<400> SEQUENCE: 1
ggcacgtctg cattgccatc gttttagagc tagaaatagc aagttaaaat aaggctagtc    60
cgttatcaac ttgaaaaagt ggcaccgagt cggtgc                              96

<210> SEQ ID NO 2
<211> LENGTH: 190
<212> TYPE: DNA
<213> ORGANISM: Artificial Sequence
<220> FEATURE:
<223> OTHER INFORMATION: Synthetic

<400> SEQUENCE: 2
gtcttctatg gcaactcgga ccgcacctcc acggttcaga acctgctgcg gcccccatc     60 atctcccgct tcatccgcct catcccgctg ggctggcatg tccggattgc catccggatg   120
gagctgctgg agtgcgtcag caagtgtgcc tgatgcctgc ctcagctcgg cgcctgccag   180
ggggtgactg                                                          190

<210> SEQ ID NO 3
<211> LENGTH: 96
<212> TYPE: DNA
```

```
<213> ORGANISM: Artificial Sequence
<220> FEATURE:
<223> OTHER INFORMATION: Synthetic

<400> SEQUENCE: 3
ggcatgtccg aattgccatc gttttagagc tagaaatagc aagttaaaat aaggctagtc    60
cgttatcaac ttgaaaaagt ggcaccgagt cggtgc                              96

<210> SEQ ID NO 4
<211> LENGTH: 190
<212> TYPE: DNA
<213> ORGANISM: Artificial Sequence
<220> FEATURE:
<223> OTHER INFORMATION: Synthetic

<400> SEQUENCE: 4
gtcttctatg gaaactcaga ccggagttct acagttcaga acttactcag gccccccatc    60
atttcccgct tcatccgact gatccctcta ggctggcacg tctgtattgc catccggatg   120
gagctgcttg agtgtgccag caagtgtgcc tgatgtctat ttcagctcag ttctgtcact   180
tgcagggaga                                                          190

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
cgtccgcatt gc                                                        12

<210> SEQ ID NO 6
<211> LENGTH: 12
<212> TYPE: DNA
<213> ORGANISM: Artificial Sequence
<220> FEATURE:
<223> OTHER INFORMATION: Synthetic

<400> SEQUENCE: 6
cgtctgcatt gc                                                        12

<210> SEQ ID NO 7
<211> LENGTH: 32
<212> TYPE: DNA
<213> ORGANISM: Artificial Sequence
<220> FEATURE:
<223> OTHER INFORMATION: Synthetic

<400> SEQUENCE: 7
cgctgggctg gcacgtccgc attgccatcc gg                                  32

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
ccggatggca atacggacat gccagcccag cg                                  32

<210> SEQ ID NO 9
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 9
ggcacgtctg cattgccatc                                              20

<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
ctctaggctg gcatgtccga attgccatcc gg                                32

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
ccggatggca attcggacat gccagcctag ag                                32

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ggcatgtccg aattgccatc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ccgtacaggc ttaacggtag                                              20
```